United States Patent [19]

Poler

[11] 4,149,279

[45] Apr. 17, 1979

[54] INTRA-OCULAR LENS STRUCTURE

[76] Inventor: Stanley Poler, 78 E. Second St., New York, N.Y. 10003

[21] Appl. No.: 865,699

[22] Filed: Dec. 29, 1977

Related U.S. Application Data

[63] Continuation-in-part of Ser. No. 780,682, Mar. 23, 1977, Pat. No. 4,080,709, which is a continuation-in-part of Ser. No. 691,033, May 28, 1976, Pat. No. 4,073,014.

[51] Int. Cl.² ............................ A61F 1/16; A61F 1/24
[52] U.S. Cl. ......................................... 3/13; 206/0.83; 206/5.1; 206/438
[58] Field of Search ................ 3/13, 1; 206/438, 0.83, 206/5.1

[56] References Cited

U.S. PATENT DOCUMENTS

| | | | |
|---|---|---|---|
| 2,834,023 | 5/1958 | Lieb | 3/1 |
| 3,028,949 | 4/1962 | Sohosky | 206/0.83 |
| 3,925,825 | 12/1975 | Richards et al. | 3/13 |
| 3,975,779 | 8/1976 | Richards et al. | 3/13 |

OTHER PUBLICATIONS

"Artiphakia and Aniseikonia" by Richard C. Troutman, American Journal of Ophthalmology, vol. 56, No. 2, Oct. 1963, pp. 602–639.

*Primary Examiner*—Ronald L. Frinks
*Attorney, Agent, or Firm*—Hopgood, Calimafde, Kalil, Blaustein & Lieberman

[57] ABSTRACT

The invention contemplates improved structure for use in making lens implants in ophthalmological surgery, the lens being a replacement for a cataract-clouded natural lens, and the replacement being installed in the pupil at the iris as the operative step following removal of the cataracted lens. The invention features adapter-element structure assembled or adapted for assembly to an intra-ocular lens element and having plural radially outward iris-stabilizable feet. The adapter-element structure is severably united to further material which aids in handling and storage, in readiness for later surgical use.

18 Claims, 20 Drawing Figures

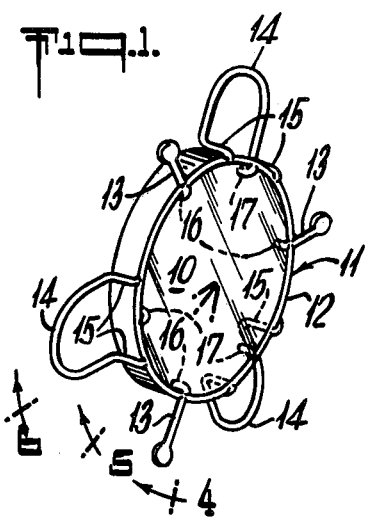
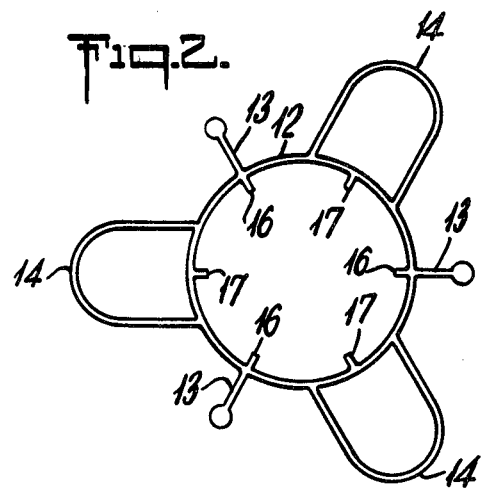
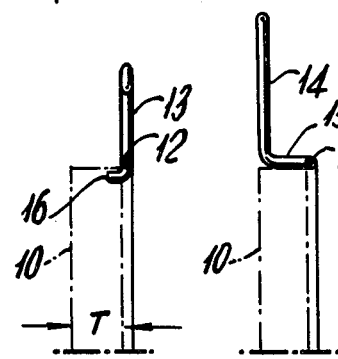
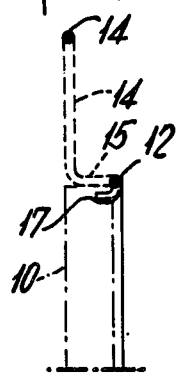
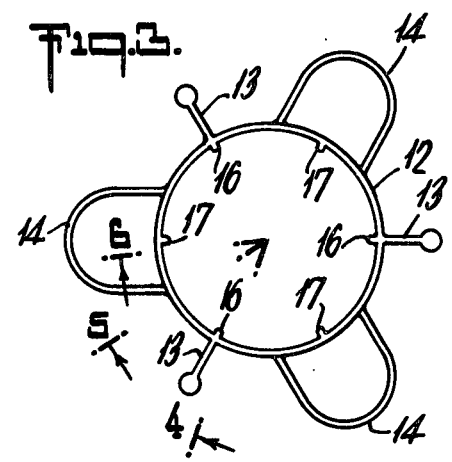
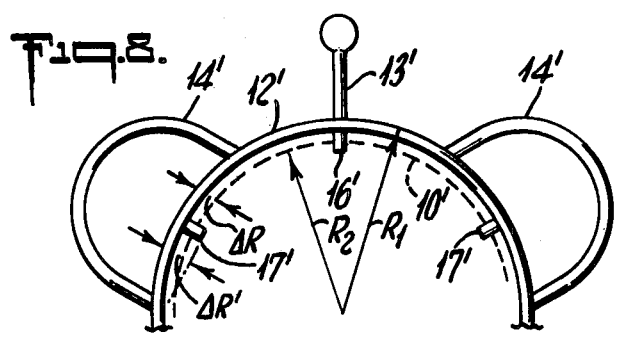
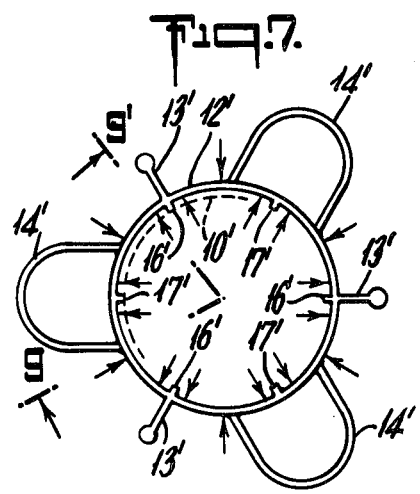
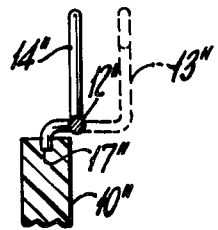

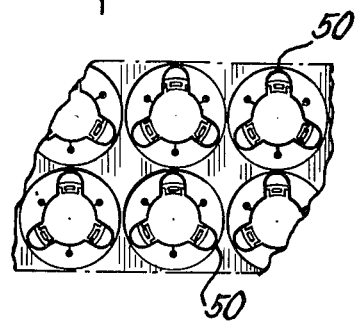
Fig.15.
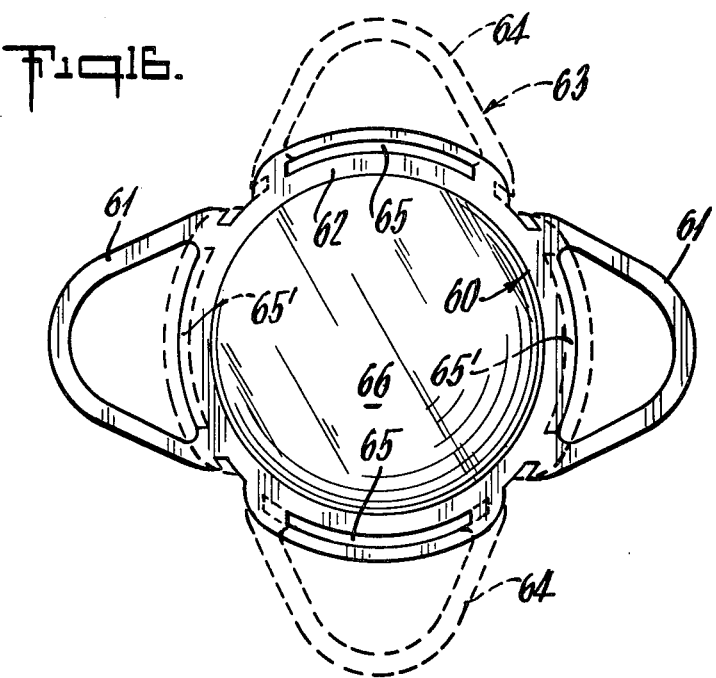
Fig.16.
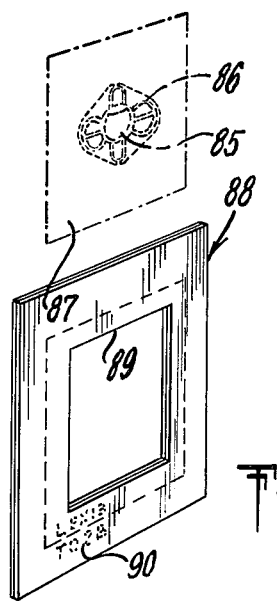
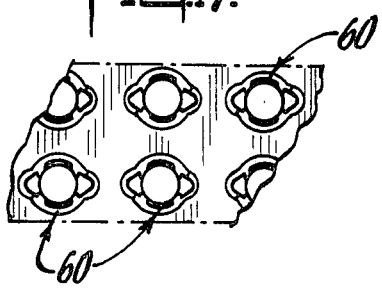
Fig.17.
Fig.20.

INTRA-OCULAR LENS STRUCTURE

This application is a continuation-in-part as to subject matter that is non-elected in my copending application, Ser. No. 780,682, filed Mar. 23, 1977, now U.S. Pat. No. 4,080,709 said copending application being a continuation-in-part of my parent application, Ser. No. 691,033, filed May 28, 1976, now U.S. Pat. No. 4,073,014.

The invention relates to improved structure for surgical use in implanting a lens, as a replacement for a cataract-clouded or otherwise diseased natural lens.

As many as 500,000 Americans a year require surgery for removal of a natural lens which has become opaque (cataract), causing loss of vision. The modern therapy for cataract is surgical removal; this is generally done either by gently lifting the opaque lens from the eye in one piece, or by fragmenting the lens and washing out the fragments. When the cataractous lens is removed, an alternate method must be provided to focus light entering the eye, so that a sharp image focuses at the retina. Strong spectacle lenses and contact lenses are both commonly used for this purpose, but both have important shortcomings. Strong spectacle lenses tremendously enlarge the image, foreshorten distances, restrict peripheral vision, and prevent both eyes from being used simultaneously if both eyes have not had cataract surgery; contact lenses overcome some of these problems but introduce others, involved in insertion, removal and frequent maintenance.

The concept of implanting an intra-ocular lens in place of the removed natural lens is not new, although it is of relatively recent origin. To date, however, a significant limitation on such a procedure has been the relative unavailability of implant lenses, for their production has relied upon small, craft-style workshops, and lens quality has been less than satisfactory.

It is an object of the invention to provide improved structure for making intra-ocular lenses, for implant procedures of the character indicated.

Another object is to provide mounting structure for such lenses, whereby operative procedures may be more safely and reliably performed, and whereby preassembled and classified mounted lenses may be more readily stored and handled, in readiness for later surgical use.

It is also an object to provide such structure as to inherently enable high product quality, adherence to specifications, and reproducibility by precision mass-production techniques.

Other objects and various further features of novelty and invention will be pointed out or will occur to those skilled in the art from a reading of the following specification, in conjunction with the accompanying drawings. In said drawings, which show, for illustrative purposes only, preferred forms of the invention:

FIG. 1 is an enlarged view in perspective, showing an intra-ocular lens and unitary mount of the invention, ready for operative implantation, as in the course of a cataract operation;

FIGS. 2 and 3 are plan views of the unitary mount of FIG. 1, FIG. 2 being to show an interim formative condition, and FIG. 3 showing the fully formed mount ready for assembly to the lens element;

Figure 11:
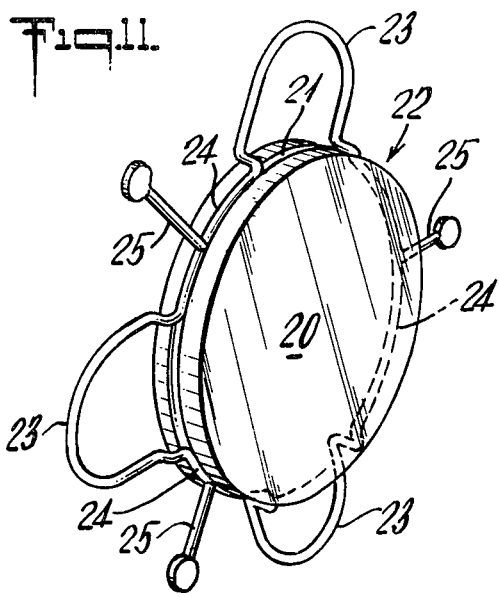
Figure 12:
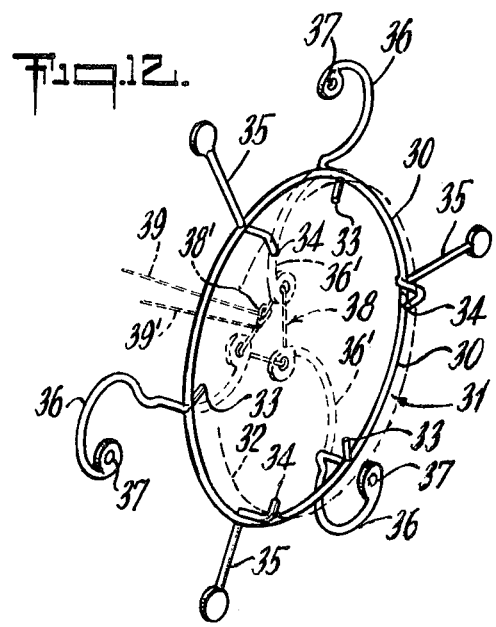
Figure 13:
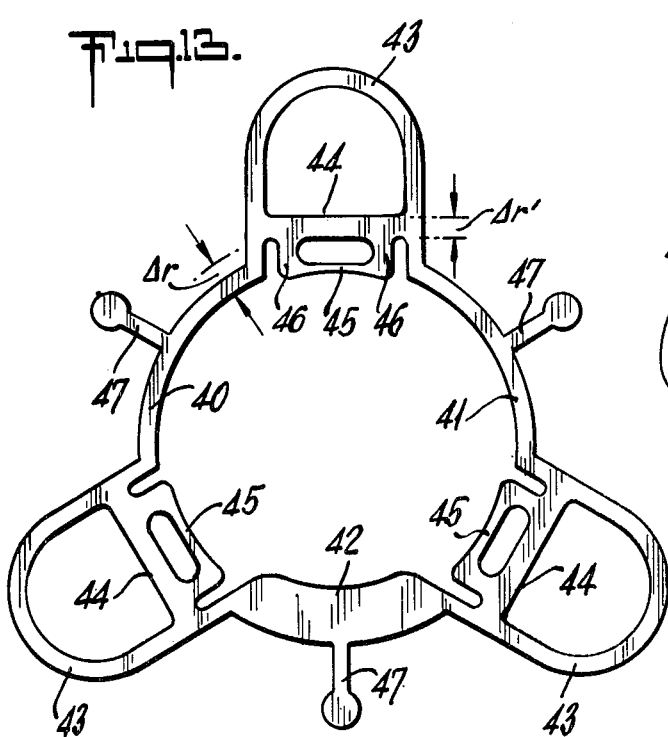
Figure 14:
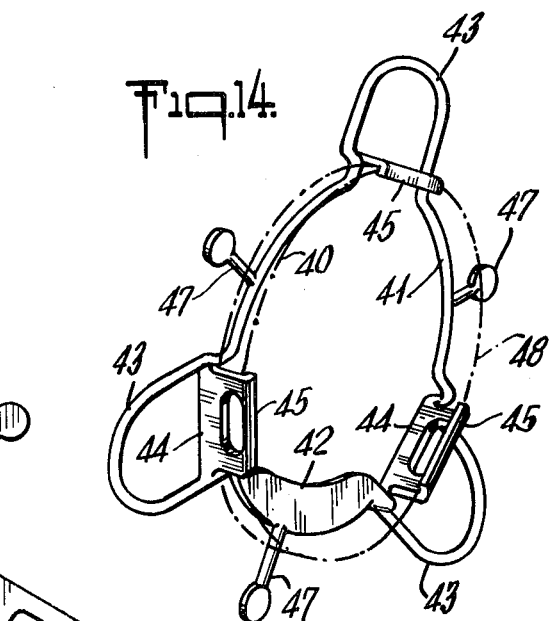
Figure 14A:
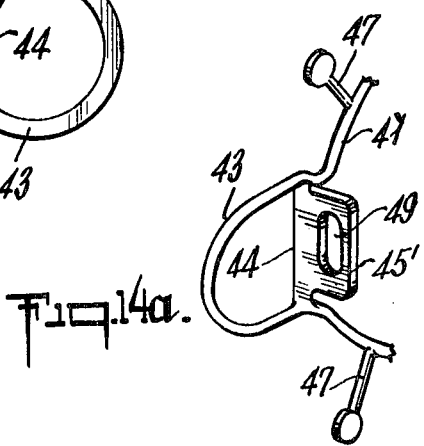
Figure 18:
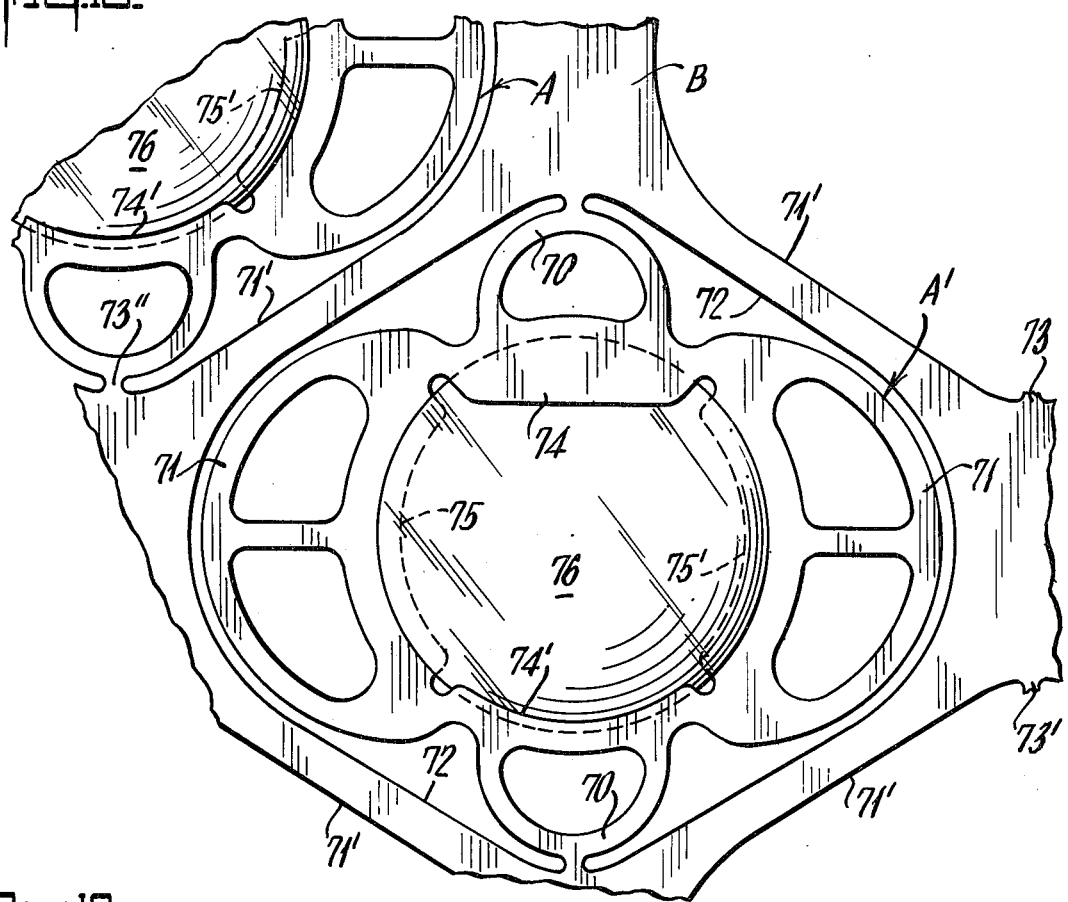
Figure 19:
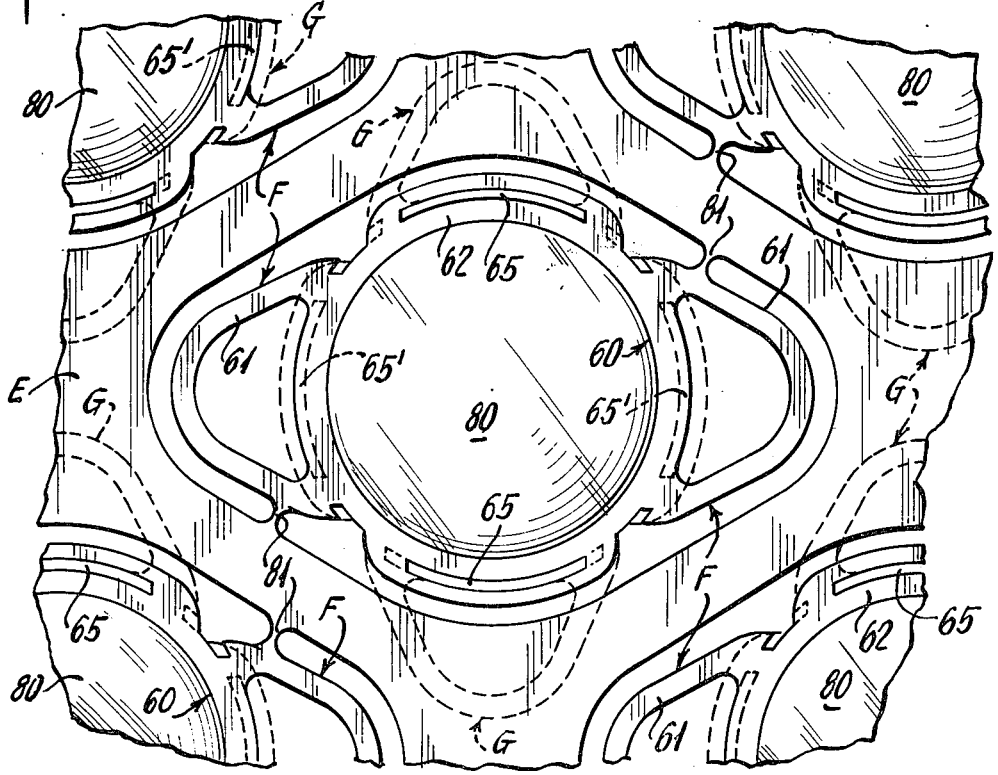

FIGS. 4, 5 and 6 are fragmentary sectional views taken at the planes 4, 5 and 6 indicated in FIGS. 1 and 3;

FIG. 7 is a view similar to FIG. 3 to show a modification;

FIG. 8 is an enlarged fragmentary view of the structure of FIG. 7, to permit identification of dimensional features;

FIG. 9 is a fragmentary sectional view, with solid outlines as taken at the plane 9, and with phantom outlines as taken at the plane 9' of FIG. 7;

FIG. 10 is a view similar to FIG. 9 to show a modification;

FIGS. 11 and 12 are perspective views to show further modifications;

FIGS. 13 and 14 are plan and perspective views to show the blank form and the ultimately bent configuration of a mounting that is particularly adapted to manufacture from a plastic material;

FIG. 14A is a fragmentary view similar to FIG. 14, to show a variation;

FIG. 15 is a fragmentary plan view of a photographically duplicated plurality of lens-mount blanks, in side-by-side severably connected multiple;

FIGS. 16 and 17 are plan and fragmentary plan views similar to FIGS. 14 and 15, to illustrate another application of the method of the invention;

FIG. 18 is an enlarged fragmentary plan view of a sheet of severably interconnected lens-mounting blanks, with mounted lens elements;

FIG. 19 is a view similar to FIG. 18, to show another embodiment; and

FIG. 20 is a simplified and exploded perspective view to illustrate a further embodiment.

Referring to FIGS. 1 to 6, the invention is shown in application to an implant lens 10 of non-toxic transparent plastic, such as methylmethacrylate. Lens 10 is of such refractive index and is so ground that when mounted at the iris and immersed in the intra-ocular, the thus-implanted eye will develop sharp image focus at the retina. Lens 10 is typically although not necessarily circular about its optical axis; it may, for example, be of 5-mm diameter and have a peripheral-edge thickness T of 1-mm or less.

In accordance with the invention, unitary mounting structure 11 is secured to lens 10 and provides first and second pluralities of radially outward feet for axially stabilized positioning reference to the iris, the feet of one plurality being axially offset from and angularly interlaced with those of the other plurality, so that both sides of the iris contribute to stability. As shown, a circumferentially continuous ring 12 conforms to the peripheral contour of the edge of lens 10, being positioned adjacent one face of the lens. The first plurality of feet comprises three angularly spaced rods 13 extending radially outward for retention adjacent the outer side (anterior surface) of the iris, with the pupilary border of the iris itself closing upon the circular edge of the lens. The second plurality of feet comprises three radially outward loops 14 in a radial plane which is axially offset from ring 12, to substantially the extent T. Thus, each of the feet 14 includes two spaced short offset leg portions 15 which engage the circular edge of lens 10, and the radial loop portion extends from the leg portions 15. For the case of the plastic lens 10 of FIG. 1, six L-shaped anchoring prongs 16-17 extend first radially inwardly and then axially rearwardly, the same being embedded into adjacent rim regions of the lens 10.

The described mounting structure or adapter 11 may be a single piece of metal, with all anchoring prongs 16-17 and stabilizing feet 13-14 integrally formed with the body ring 12. The metal is inert a body tissue and fluids and is suitably stainless steel, of thickness in the order of 0.1-mm. I have found it practical to construct the "blank" of FIG. 2, for the mounting structure 11, by employing photographic and etching techniques.

More specifically, for the case of the "blank" of FIG. 2, a drawing was initially prepared, to greatly enlarged scale, e.g., 40 times. This drawing was photographically reduced to ultimate size, and multiplied at indexed locations to produce a photographic negative with plural reduced images of the drawing. Then, one of a class of metals which was tolerated by the body (e.g., stainless steel, platinum, irridium, etc.) was coated with a photosensitive material. The negative was placed in contact with the photosensitive coat, exposed to light, and then developed in a "photographic reversal," thus removing from the exposed surface those areas which have been exposed to light. The sheet that was left was then placed in a chemical solution (ferric chloride) which etched away unwanted material, leaving only a completed profile of the "blank." The described etching process has the advantage that it tends to produce round, burr-free edges, and it can use materials that are lighter and thinner than anything which to my knowledge and belief has been available to date.

FIG. 2 depicts the "blank" thus prepared, it being noted that lobes 14' are of extended radial projection, in order to account both for the offsets 15 and the loops 14; by the same token, the barbs 16'-17' are of extended inward radial projection, in order to account for both the radially inward and the axially inward leg portions of prongs 16-17. Bending dies are employed to operate upon the "blank" of FIG. 2, such that all necessary axial offsets are produced, resulting in reduction of the overall circle defined by legs 14 and expansion of the circle defined by prongs 16-17, all as appears from comparison of the "before" and "after" plan views of FIGS. 2 and 3.

To complete the description of an actual physical embodiment of FIGS. 1 to 6, I indicate that each of the retaining rod-like feet 13 terminates with a small knob formation, to avoid presentation of any sharp edge to irritate iris tissue. These knobs are on a circle of 7.5-mm diameter, and the outer limits of legs 14 are on a circle of 8-mm diameter. The prongs 16-17 are bent axially at a location radially inwardly offset about 0.15-mm from the body ring 12; they are embedded into lens 10 to the extent of about 0.3-mm in the axial direction. Such embedding may be accomplished without drilling, by axially directed ultrasonic driving impulses applied at prongs 16-17, while retaining ring (12) and leg (13-14) parts of the adapter 11 in damped condition. The optical distortion of lens 10 due to such driven assembly of the adapter to the lens is negligible.

In the embodiment of FIGS. 7 to 9, the layout of the adapter "blank" is generally as described for FIG. 2, with the exception that the radius $R_1$ of the body ring 12' exceeds the radius $R_2$ of the lens 10' about its optical axis to an extent $\Delta R$ which is slightly less than the effective radially inwardly projecting extent $\Delta R'$ of the anchoring barbs 14'-17'. The interlaced pluralities of radially outward stabilizing feet 13'-14' are in axially offset relation, each plurality being offset in the direction opposite the other plurality, as is apparent from FIG. 9. To assemble the adapter of FIG. 7 to its lens 10', the body ring 12' is transiently distorted by suitable tooling, in approach to a polygonal shape; the action of such tooling is denoted by radially inward and radially outward arrows which symbolize local force application to transiently radially outwardly displace all barbs 16'17' to clear the outer-edge on rim radius $R_2$ of lens 10'. Once axially centered around this rim, the tooling is relaxed to allow compliant restoration, barbs 16'-17' contact the lens rim and are then driven into short radial local embedment in the lens, as by ultrasonic tool means. The assembly is then complete and ready for sterilization and implantation.

FIG. 10 illustrates a slight modification of FIGS. 7 to 9, wherein the ring body 12" is at one axial end of lens 10" and the pluralities of stabilizing feet 13"-14" determine iris retention in a plane that is axially offset from lens 10". The barbs 16"-17" are longer than previously described, to permit an axially offsetting projection from ring 12" before radially inward bending to engage and become locally radially embedded at spaced locations along the rim of lens 10".

In the embodiment of FIG. 11, the rim of lens 20 has a peripheral groove 21, and the unitary mounting adapter 22 is so formed as to permanently assemble by resilient snap action into the groove 21. Adapter 22 may still be formed from a single piece "blank" by the indicated photo-chemical technique, and it may still be a circumferentially continuous structure. As shown, the looped legs 23 comprising one plurality of locating feet integrally connect adjacent ends of spaced body-ring arcs 24, and the rod-like feet 25 of the other plurality extend radially from the respective arcs 24; axial offset of these pluralities is built into legs 23, in the manner generally as described at 15 in FIG. 1, except for a small initial radially outward offset in such legs 23 at juncture with arcs 24. In unstressed condition, the arcs 24 are of curvature conforming to that of groove 21 and are preferably at a slight radially inwardly displaced position with respect to the circle of groove 21. To assemble to lens 20, arcs 24 are outwardly spread against the compliant action of loops 23, in order to permit placement and resilient snap retention of arcs 24 in groove 21. The assembly is then ready for sterilization and implantation.

In the embodiment of FIG. 12, the circular body ring 30 of a unitary adapter 31 is retained in its assembly to a lens 32 by radially inward barbs 33-34 of one plurality (33) which engage over one axial end of lens 32 and of another plurality (34) interlaced with the barbs of the first plurality and engaging over the other axial end of lens 32, thus retaining the assembly without resort to mechanical embedment in lens material.

As shown, the iris-stabilizing feet 35 of one plurality are spaced radial rods at the ring locations of barbs 34, and barbs 34 include axial offsets to the extent of lens-rim thickness. The feet 36 of the other plurality include axial offsets at juncture with the body ring 30, at which locations barbs 33 also extend radially inward. Feet 36 differ from the loops already described in that they are somewhat coiled or looped in a common radial plane, the free end of the coil being apertured at 37. FIG. 12 will be understood to depict the unstressed normal condition and orientation of feet 36.

In accordance with a feature of the invention, the inherent resilient compliance of feet 36 and their apertured ends 37 are employed to facilitate operative insertion through the pupil of the iris. In preparation, a suture 38 such as a filament of nylon is tied with a loop 38' intermediate its free ends 39-39'. The end 39 is threaded through all foot apertures 37 before passing through loop 38' and is then tightened, to radially inwardly compliantly draw all foot ends 37 to within the peripheral confines of lens 30, as denoted by phantom outlines 36' in FIG. 12. In operative insertion of the retracted legs 36 past the pupil, the suture ends 39–39' are held back, the end 39 being tightly held until release when legs 36 are safely behind the iris. Upon release of the end 39, the other end 39' is drawn, thereby first withdrawing the loop 38' and allowing the remaining end 39 to pull out of loop 38' and all apertures 37 before complete removal of the suture.

FIGS. 13 and 14 depict another lens-mount embodiment of the invention wherein the ring-like body comprises plural spaced arcuate spans 40–41–42 between integrally connected loops 43, and wherein at each loop a short bridge 44 (at a radial offset Δr, with respect to the circle of body arcs 40–41–42, in the blank of FIG. 13) connects the spaced legs of the loop and circumferentially strengthens the circumferential integrity of the body. Radially inwardly extending from each bridge 44 is a lens-retaining formation 45, effectively isolated from the associated bridge 44 except for arcuately spaced integral leg connections 46 thereto. The rod-like feet 47 of previously described embodiments radiate centrally form each of the body arcs 40–41–42.

The blank of FIG. 13 is bent by suitable tooling into the lens-retaining configuration shown in FIG. 14, wherein it is seen that the projections 45 have been axially offset from the plane of body arcs 40–41–42, so that the respective axial limits of the periphery of the lens element (suggested by phantom outline 48) are engaged to permanently retain the lens to its mount. The relatively substantial radial extent Δr' by which bridge 44 is connected to the legs of each loop 43, in the context of the relatively torsionally compliant nature of connection of each loop 43 to its adjacent body arc (40–41–42) will be understood to enable transient radially outward manipulation of any of the lens-engaging projections 45 merely by axially deflecting one of the loops 43, thus readily permitting insertion of and engagement to a lens 48 at its rim.

To complete the description of FIG. 14, the loops 43 will be seen also to have been subjected to bending, such that each bridge element 44 extends axially to provide an axial offset for the radial plane of loops 43 with respect to the radial plane of feet 47, so that loops 43 and feet 47 may engage opposite sides of a supporting iris.

Also shown in FIGS. 13 and 14 is the provision of a singularly wide body-arc element at 42, for identification purposes, e.g., manufacturer's mark, lens-identifying code, and date of manufacture.

Thus far, the invention has been described in the particular context of using a metal as the material of the lens-mounting structure. This is not to be taken as precluding the use of other materials, as for example a suitably inert plastic, such as nylon or polypropylene. In a preferred employment of a film sheet of nylon or a high-temperature polyimide (e.g., Kapton, a product of E. I. DuPont Company), very much the same etching technique may be employed as above indicated for the case of an etched sheet of metal. This close similarity will appear from the following Example I, being a specific recital of steps to produce the plastic article.

EXAMPLE I

1. A sheet of nylon or polyimide film is selected 0.002 to 0.005-inch thick, being the same thickness range as used in the etched-metal technique described above. The selected plastic sheet is tested for water content, mechanical strength, and spectrographically for fidelity of composition.

2. The sheet is washed in acetone and is then air-dried.

3. The sheet is washed in distilled water and is then air-dried.

4. The sheet is visually inspected for cleanliness and surface defects.

5. The sheet is prepared for a photo-resist coating by vacuum or other deposition of chromium.

6. A photo-resist coating of photographic emulsion is applied to both sides of the sheet and is then allowed to air-dry.

7. By first preparing a drawing at 20X to 50X scale, and then photographically reducing it, in steps as necessary, culminating in reproduction onto a glass photographic plate, a master negative is made to ultimately desired scale; preferably, the master negative includes a plurality of duplicates of the same photographically reduced drawing, in side-by-side adjacency and with interconnected leg formations, as will appear for the tangential rod-like connections 50 to legs of the configuration repeated in FIG. 15.

8. The nylon or polyimide film sheet is placed in a vacuum frame to flatten and hold it tight against a glass platten, and the master negative is photographically exposed to both sides of the sheet, with accurate registry.

9. The exposed sheet is developed, with the result that area are not developed where masked by the negative and, therefore, not exposed to light. The areas reached by light are washed away by the developer, and in the case of a polyimide sheet, there may be an initial etching action attributable to the developer.

10. The developed sheet is fixed.

11. The sheet is etched, hydrazine hydride being used for the etching of nylon or polyimide sheet, and being usable for certain other plastic materials.

12. The photo-resist is washed away, using either a plasma process or a fluorocarbon cleaner.

13. The resulting lens-mount sheet of severably connected part blanks is then dipped in a 30 percent solution of hydrazine hydride, to round-off edges of the parts.

14. The sheet of otherwise-finished parts is degassed, by increasing sheet temperature to 300° F. in the case of nylon, or 500° F. for the case of high-temperature polyimide.

15. The mounting rings are cut free from the sheet, at 50, to create individual ring blank parts, as in FIG. 13.

16. Individual ring parts are mechanically bent to profile, as appears in FIG. 14, and the profile is inspected.

17. A glass or molded-plastic lens is selected and mounted, as appears from the phantom-outline relation in FIG. 14.

18. The total assembly is inspected, and the assembly is marked, with serial number and code, at 42 in FIG. 14.

19. Final inspection is performed.

20. The total individual assembly is plasma-cleaned and packaged, and then gas or autoclave-sterilized.

21. Final inspection is performed through the package window, and the package is marked, as to date and lot.

A totally different photo-etch or other erosion technique is also applicable to manufacture of lens-mounting adapters of the present character, particularly for the case of such adapters formed from plastic sheet, as will appear from the following Example II.

EXAMPLE II

1. Two matching metal masks or master sheets, for example of aluminum, are prepared as in accordance with the photo-etch technique described above.

2. A sheet of suitable plastic, such as nylon or polyimide film, is selected, 0.002 to 0.005-inch thick, and is subjected to tests, washing and drying as noted at steps 1 to 4 of Example I.

3. The metal master sheets as cement-laminated to the front and back surfaces of the plastic sheet, in precise register.

4. The plastic-sheet laminate, thus masked, is exposed to the discharge of a plasma generator or micro-ion mill, in the presence of a suitable reactive gas, for example for one hour, until the desired configuration has been generated by erosion of unmasked regions of the plastic material.

5. The cement is dissolved to permit removal of the aluminum masks or master sheets for cleaning and re-use.

6. The configurated plastic sheet has the appearance of FIG. 15 and may be cleaned by further exposure as in Step No. 4 of this Example II, for example for an exposure time of approximately two minutes, to remove any possible organic debris and burrs.

It will be seen that I have described intra-ocular lens and mount structures meeting all stated objects, and, importantly, lending themselves to mass-production techniques, of inherent precision and control. The drilling operations previously considered necessary have been totally avoided, as has also the reliance upon multiple parts, thus simplifying manufacturing and avoiding generation of waste particles. While plastic lenses have been specifically mentioned in several illustrative contents, it will be appreciated that the invention is not necessarily limited to such use. For example, glass lenses are to be preferred and certainly can be well and safely mounted, using structures of FIGS. 11 to 14. Also, although circular lens body-ring peripheral contours have been described for all forms, it will be appreciated that this was purely to simplify description, in that the described techniques and structures have equal application whatever the peripheral contour of the lens; for example, an oval lens-rim contour may be selected for more ready operative insertion past the pupil, for certain patient requirements, and to reduce the chance of surgical trauma. Still further, the inherent nature of the mounted lenses of the invention is such that an absolute minimum of structure ever protrudes into the anterior chamber of the eye; thus, danger of corneal-tissue contact with any part of the intra-ocular lens structure of the invention is substantially less than that with prior art structures. For the disclosed forms of the invention wherein the iris closes on a circular lens periphery, there is minimal stress on the sphincter muscle, with attendant reduced risk of trauma.

In the discussion thus far, it has been indicated that the lens element accommodated by my mounting-ring adapter may be of a glass or plastic material, the implication being that the lens element is a separate article of manufacture, later assembled to its mount. However, it will be appreciated that every one of the described mounting-ring embodiments is applicable to placement in a suitably formed lens-molding cavity such that at least the lens-retaining part of the mounting ring is embedded in a plastic lens element that is injection-molded in the cavity. The blank of FIG. 13 lends itself particularly well to such use at the time of injection-molding the lens element, in that the lens-retaining extension 45 need not be bent radially, as shown in FIG. 14, but rather may merely be bent axially, as shown at 45' in FIG. 14A, in which case injection-molding lens material may be forced in the molding process to enter the slot or opening 49 between bridge 44 and extension 45. Thus-molded, the lens element will be positively keyed and located by radially outwardly formed lens material at each of the openings 49.

It has also been indicated above that the preferred process of etching developed regions of a photographically reduced lens-mount master negative lends itself to quantity production of pluralities of such lens mounts, in adjacent multiple as suggested in FIG. 15. And such production lends itself to further options in regard to assembly with plastic lens elements. In one procedure, the individual mounting blanks are severed at 50 and are then bent to form lens-retaining projections, as described at 45' in connection with FIG. 14A; the individual mount, thus-prepared, may then be assembled to the lens-molding cavity for localized embedding in the lens material in the course of injection-molding the lens. Alternatively, the lens-retaining projections 45' may be bent out of all lens-mount structure in a large plurality on a single sheet, prior to severance at 50; in the event, and with the sheet of thus-formed lens mounts suitably introduced to a multiple-cavity mold for simultaneously molding a similarly spaced plurality of lens elements, all of the plural lens-and-mount assemblies may be completed in a single injection-molding step, i.e., a single injection-molding of all lens elements, each into assembled relation with its own mount. Thus formed, the plural assemblies are conveniently handled, shipped and stored as a single sheet, with severance of individual assemblies at 50, only when and as needed.

While the invention has been described in detail for the preferred forms shown, it will be understood that modifications may be made within the scope of the invention. For example, the reference to metal for the adapter structures of FIGS. 11 and 12 will be understood to be illustrative, since similarly formed and suitably stiff and non-toxic plastics may also serve the same purpose. Also, the reference to photo-chemical preparation of metal "blanks" is illustrative of a preferred technique, in that photo-resist and plating techniques of the printed-circuit technology, with subsequent release from a substrate, may also be employed; and the use of positive and negative terminology in reference to photographic processing will be understood to be illustrative and not limiting, in that reversal development techniques for proceeding from positive original, directly to a positive-developed image, are also to be understood as applicable.

Also, while metal-ring structures have been disclosed in combination with the lens element thereby mounted, it will be understood that such unitary structures may be, and in certain cases preferably are, subjected to an inert protective coating of a plastic material such as nylon, thus assuring against any possibility of a minute metal burr or barb projecting for body-tissue contact. By the same token, the described plastic-sheet embodiments and methods will be understood to relate to basic structural formations and not necessarily to be concerned with such final coating or finishing as may be desired for particular purposes; for example, a coating of inert material, such as vacuum-deposited or sputtered Teflon or platinum may be applied to an otherwise-finished configurated adapter element, to provide enhanced assurance of a non-toxic ultimate product.

Still further, it will be understood that although all mounting adapters thus far described have been of single-piece unitary construction, the described methods of manufacture are also applicable to multiple-piece mounting adapter, such as the two-piece configurations disclosed in greater detail in my patent application, Ser. No. 780,445, filed on even date with said Ser. No. 780,682. The basic blank element, i.e., for one half of such structure, is shown at 60, in solid outline in FIG. 16, with its two mounting lobes 61 projecting radially outward of its ring-like body 62, by diametrically opposed locations; another such element 63 is shown in phantom outline with its two mounting lobes 64 in angularly interlaced relation with lobes 61. The lobes (61) of one adapter element (60) and the lobes (64) of the other adapter element (63) are retained in slotted interlobe regions 65-65' of the respective elements 60-63, and the thus-assembled adapter elements uniquely locate and retain a lens 66; when inserted in the eye, the lobes 61 stabilize the assembly with reference to one side of the iris, and the lobes 64 provide stability with reference to the other side of the iris. The nature of the material of the elements 60-63 should be such that at least the lobes to be inserted past the iris are resiliently compliant, and highly satisfactory assemblies may be made wherein both adapter elements 60-63 are duplicates of each other, formed of suitable plastic such as nylon or polyimide sheet, according to methods as described above at Example I and Example II. Thus a single multiple-element sheet, a fragment of which is shown in FIG. 17, may be prepared to serve the mounting-adapter element (60-63) purposes of a plurality of FIG. 16 assemblies. It is to be understood, furthermore, that chemical etching and mechanical, electronic or other erosion are to be deemed equivalent manipulative steps, depending upon the manufacturing approach and selected materials involved.

Beyond the multiple-molded arrangement described above in connection with FIG. 15, involving a single sheet of severably interconnected mounted lenses, it will be appreciated that a single sheet (as in FIG. 15) also lends itself to accommodation of separately formed finished lens elements assembled and retained in multiple, and whether the finished lens elements are of glass or plastic. Specific examples of such sheet material, with one or more prefinished lens elements assembled thereto, are shown in FIGS. 18 and 19, for the case of single-part adapter mounts and for the case of two-part adapter mounts, respectively.

In FIG. 18, the unit adapter mount is shown in full for the case of mount A, which will be recognized to be that shown in FIG. 3 in said application Ser. No. 780,445. This adapter mount is shown to be formed in spaced multiple from a single sheet of material B, to portions of which mount A is severably connected at the extremities of iris-stabilized foot elements 70. The mount A includes further iris-stabilized feet 71 and is otherwise contained within an opening having an inside edge 72 which is spaced from but generally follows the contour of the periphery of mount A. Initially, the mount A is formed from sheet B in plural spaced array, edge contours for similar openings accommodating four further units of the array being identified at 71'. For the situation depicted in FIG. 18, three of these further mounts A have been removed, by breaking their points, as at 73-73', of severable connection to sheet B; the fourth of these additional mounts remains in place and is identified as mount A', being shown with an unsevered connection 73" to sheet B. Each mount A-A' has plural radially inward lens-retaining lug or tab formations 74-75-74'-75' engaging opposite axial sides of the periphery of a finished lens element 76, so that all finished and thus-mounted lenses 76 can remain in easily handled and storable condition, as parts of sheet B, until severed (as at 73') at or just prior to need as a surgical implant.

The situation depicted in FIG. 19 resembles that described for FIG. 18, except that the lens elements 80 are retained assembled to the single sheet E by means of the two-piece mount structure described above in connection with FIG. 16. For each mounted lens element 80 in FIG. 19, the mounting structure comprises a first mounting element F which has integral but severable connection to sheet E, at spaced points 81; and a second mounting element G (which is a duplicate of mounting element F) has been severed from another sheet E of multiple mounts to permit individual assembly to its particular lens 80 and unsevered mount F. Such assembly will be understood to be as described in connection with FIG. 16, all except for the fact that mount elements F are not initially severed from sheet E. Thus, a sheet E with assembled lenses 80 according to FIG. 19 may have all the storage and handling features mentioned above for other embodiments.

In FIG. 20, I illustrate application of the invention to the individual carded or otherwise framed mounting or packaging of an adapter-mounted lens, the same being suggested by phantom outline at 85 and retained by a single-piece mount 86 which is severably connected to a rectangular surrounding body 87 of the sheet material from which mount 86 is formed. The thus-mounted lens 85 is framed by reinforcement material which may comprise the two registering halves of a projection-slide assembly 88, the periphery of the body 87 of sheet material being retained by and between the adhered halves of frame 88, in position to expose but protect the lens 85 and its mount 86 within the frame opening 89.

It will be understood that the individual framing technique illustrated by FIG. 20 lends itself not only to convenient handling and storage of a finished and mounted lens 85, until severance for implantation, but that the framing 88 enables ready optical evaluation and double-checking of the properties of lens 85 at any time, merely by removable insertion of frame 88 in slide-holding means (not shown) of conventional construction, associated with the particular optical instrumentation; and identifying notations including measured optical properties may be marginally entered on a face of frame 88, as suggested at 90. It will also be understood that in FIG. 20, the frame-mounting of an individually assembled lens 85 is illustrative for a variety of adapter-mount configurations, including the style of two-piece adapter mounting illustrated in connection with FIG. 19.

What is claimed is:

1. As an article of manufacture, a single sheet of duplicates of a lens-mounting blank, in side-by-side adjacent array, each of said blanks comprising a single ring-like body and a plurality of angularly spaced radially outwardly projecting iris-stabilizing feet, each body being radially inwardly configured for lens-engagement, adjacent blanks of said array being severably interconnected via at least one of the iris-stabilizing feet of each mounting blank.

2. The article of claim 1, in which an intra-ocular lens element is in assembled relation to the lens-engageable formations of each of a plurality of adjacent mounting blanks of said plurality.

3. The article of claim 2, in which each lens element is a unitary fabricated element assembled as a unit to said lens-engageable formations, and retained as a severable one of a plurality of similar parts of said sheet.

4. The article of claim 2, in which each lens element is of injection-molded plastic with said lens-engageable formations embedded in said plastic.

5. The article of claim 4, in which the lens-engageable formations comprise at each mounting blank a radially inward tab with an anchoring aperture therein, said tab being bent axially out of the plane of said blank, and said lens element being molded with lens material extending into the tab apertures of said lens-engageable formations.

6. The article of claim 1, in which said sheet is of metal.

7. The article of claim 1, in which said sheet is of plastic material.

8. The article of claim 2, in which said lens element is of glass.

9. The article of claim 2, in which said lens element is of plastic.

10. The article of claim 2, in which each lens element is prefinished, and in which each body alone retains its lens element in assembled relation thereto.

11. The article of claim 1, in which the radially inward configurations of each body are alone sufficient to engage and retain a single finished and assembled lens element.

12. The article of claim 1, in which each body is configurated to constitute one of two interengageable halves of a lens-mounting blank.

13. The article of claim 12, in which a severed one of said halves is assembled to an unsevered one of said halves, and in which a prefinished lens element is retained by and between said assembled halves, whereby the mounted lens element is severably retained by adjacent material of said sheet.

14. As an article of manufacture, a body of sheet material containing a lens-mounting blank formed from said material and severably connected thereto, said blank comprising a single ring-like body and a plurality of angularly spaced radially outwardly projecting iris-stabilizing feet, said body being radially inwardly configured for lens-engagement.

15. The article of claim 14, in which a prefinished lens element is assembled to and retained by said body, whereby a mounted lens may be severably retained in and handled by way of sheet material external to said blank.

16. The article of claim 15, in which said body is the only means of retaining said lens element.

17. The article of claim 15, in which said body is one of two means retaining said lens element, the other of said means being a severed duplicate of said body, and said bodies having interlocking formations external to the lens-element periphery.

18. The article of claim 15, in which a reinforcing frame is assembled to said sheet and surrounds the mounted lens element.

* * * * *